(12) United States Patent
Ho et al.

(10) Patent No.: US 10,456,781 B2
(45) Date of Patent: Oct. 29, 2019

(54) FLUID INSPECTION DEVICE

(71) Applicant: SKYLA CORPORATION HSINCHU SCIENCE PARK BRANCH, Hsinchu (TW)

(72) Inventors: Szu-Hsien Ho, Hsinchu (TW); Chia-Chun Wei, Taichung (TW); Hung-Wei Chen, Taichung (TW)

(73) Assignee: SKYLA CORPORATION HSINCHU SCIENCE PARK BRANCH, Hsinchu (TW)

( * ) Notice: Subject to any disclaimer, the term of this patent is extended or adjusted under 35 U.S.C. 154(b) by 88 days.

(21) Appl. No.: 15/346,326

(22) Filed: Nov. 8, 2016

(65) Prior Publication Data
US 2017/0282175 A1 Oct. 5, 2017

(30) Foreign Application Priority Data
Mar. 29, 2016 (CN) .......................... 2016 1 0186901

(51) Int. Cl.
*B01L 3/00* (2006.01)
*G01N 33/52* (2006.01)

(52) U.S. Cl.
CPC .......... *B01L 3/502* (2013.01); *B01L 3/50273* (2013.01); *B01L 3/502723* (2013.01); *G01N 33/52* (2013.01); *G01N 33/525* (2013.01); *B01L 2200/0684* (2013.01); *B01L 2300/089* (2013.01); *B01L 2300/0825* (2013.01); *B01L 2300/0848* (2013.01); *B01L 2300/0851* (2013.01); *B01L 2300/0864* (2013.01);

(Continued)

(58) Field of Classification Search
CPC .............. B01L 3/502; B01L 3/502723; B01L 3/50273; B01L 2400/0406; B01L 2300/0851; B01L 2300/089; B01L 2300/0887; B01L 2300/0864; B01L 2200/0684; B01L 2300/0848; B01L 2300/0825; G01N 33/52; G01N 33/525
See application file for complete search history.

(56) References Cited

U.S. PATENT DOCUMENTS 5,938,923 A * 8/1999 Tu .................... B01D 39/2072
                                                           210/490
6,270,641 B1 * 8/2001 Griffiths ................ B01F 5/0403
                                                           204/450

(Continued)

*Primary Examiner* — Lore R Jarrett
(74) *Attorney, Agent, or Firm* — JCIPRNET

(57) ABSTRACT

The present invention provides a fluid inspection device comprising at least one channel including a top channel surface and a bottom channel surface, and a first spacing formed therebetween; at least one chamber communicating with the at least one channel from which a fluid flows into the at least one chamber and including a top chamber surface, a bottom chamber surface and a fluid-filling area and a through opening communicating with the at least one chamber and the outside. A second spacing is formed between the top chamber surface of at least one portion of the fluid-filling area and a corresponding bottom chamber surface thereof, wherein the second spacing is smaller than the first spacing. The fluid inspection device prevents bubbles from producing in the chamber and obstructing the inspection and further allows less required fluid amount in the chamber.

17 Claims, 11 Drawing Sheets

(52) U.S. Cl.
CPC .................. *B01L 2300/0887* (2013.01); *B01L 2400/0406* (2013.01)

(56) References Cited

U.S. PATENT DOCUMENTS

| | | | |
|---|---|---|---|
| 7,604,775 B2* | 10/2009 | Pollock | A61B 5/150358 422/408 |
| 2003/0007893 A1* | 1/2003 | Purcell | B01L 3/5027 422/400 |
| 2007/0166200 A1* | 7/2007 | Zhou | B01L 3/5025 422/400 |
| 2007/0183935 A1* | 8/2007 | Clemmens | B01F 11/0071 422/400 |
| 2014/0080206 A1* | 3/2014 | Dahan | B01L 3/502753 435/288.7 |

* cited by examiner

FLUID INSPECTION DEVICE

RELATED APPLICATIONS

This application claims the priority of Chinese Patent Application No. 201610186901.3, filed on Mar. 29, 2016, at the State Intellectual Property Office of the P.R.C, the entire disclosure of which is incorporated herein by reference.

FIELD OF THE INVENTION

The present invention relates to an inspection device, specifically a fluid inspection device.

BACKGROUND OF THE INVENTION

Nowadays, the subject of a fluid inspection device with channels or micro-channels is quite popular. In the general course of fluid inspection, a tested fluid enters a chamber through a channel of the fluid inspection device for mixture or reaction in the chamber. During the tested fluid enters the chamber, it is easy for bubbles to come up in the chamber before the chamber is filled with the tested fluid and then the inspection is obstructed.

Furthermore, since the internal diameters in the channel system or micro-channel system are tiny, the micro-pump or centrifugal force is usually used as a driving force to drive the tested fluid sample. However, the costs of various micro-pumps are mostly high and the stabilities thereof are not good enough. On the other hand, heat is easily generated in the course of centrifugation, which may break down the sample. Moreover, these two technique solutions cannot prevent bubbles from mixing with the sample in the channels and being trapped in the chamber.

The bubbles in the chamber dramatically influences the accuracy of values obtained by the inspection and leads to misjudgments. Current fluid inspection devices cannot prevent bubbles from forming within the chamber in a simple way. Thus, a special fluid inspection device is necessary to solve the above-mentioned problems. Moreover, it will be an advantage to reduce the amount of the tested sample when the tested sample comes from human biological samples or chemical analytes which are hard to access.

SUMMARY OF THE INVENTION

To solve the existing problems, the present invention discloses a fluid inspection device. It does not need any drivers to be the source of the driving force and can be operated easily, and the fluid inspection device can prevent the bubble from producing and being trapped in the chamber, so that the inspection result will not be interfered by the bubbles. Furthermore, the fluid inspection device can be structurally designed to minimize the necessary amount of the tested fluid so as to reduce the cost and to facilitate focusing during an optical inspection.

According to a first aspect of the present invention, a fluid inspection device is provided and includes at least one channel, at least one chamber and a through opening. The at least one channel includes a top channel surface and a bottom channel surface, wherein a first spacing is formed therebetween. The at least one chamber communicates with the at least one channel from which a fluid flows into the at least one chamber, and includes a top chamber surface, a bottom chamber surface and a fluid-filling area, wherein a second spacing is formed between the top chamber surface corresponding to at least a portion of the fluid-filling area and the bottom chamber surface corresponding to the at least a portion of the fluid-filling area. The through opening communicates with the at least one chamber and an outside.

Preferably, a surface is formed at at least one of the top chamber surface and the bottom chamber surface around the fluid-filling area to form a step between the surface and at least one of the top chamber surface and the bottom chamber surface of the at least a portion of the fluid-filling area.

Preferably, the at least one chamber further includes a lateral wall connected to at least one of the top chamber surface and the bottom chamber surface, and an interval is formed between the lateral wall and a periphery of the fluid-filling area.

Preferably, at least one of the top chamber surface and the bottom chamber surface of the at least a portion of the fluid-filling area has a paraboloid.

According to the second aspect of the present invention, a fluid inspection device is provided. The fluid inspection device includes a test strip. The test strip includes a plurality of channels, a plurality of chambers and at least one through opening. Each of the plurality of channels includes a top channel surface and a bottom channel surface, wherein a first spacing is formed therebetween. The plurality of chambers respectively communicates with the plurality of channels from which a fluid flows into the plurality of chambers, wherein each of the plurality of chambers includes a top chamber surface, a bottom chamber surface and a fluid-filling area, and a second spacing is formed between the top chamber surface of at least a portion of the fluid-filling area and the bottom chamber surface corresponding to the at least a portion of the fluid-filling area. The at least one through opening communicates with the plurality of chambers and an outside.

The fluid inspection device of the present invention provides an embodiment having multiple channels and multiple chambers. With an configuration arrangement of the initial end of every channel connecting to each other, an user is allowed to inject the tested fluid into the multiple channels in one operation. In the situation that the same tested fluid needs to be inspected with multiple times or various tests, this configuration can reduce the frequency of operating so as to be more time-saving. Since it needs only a one-time injection during operation, a bias coming from a human error can also be greatly reduced.

The present invention will be more clearly understood through the following descriptions with reference to the drawings:

DETAILED DESCRIPTION OF THE PREFERRED EMBODIMENTS

Figure 1A:
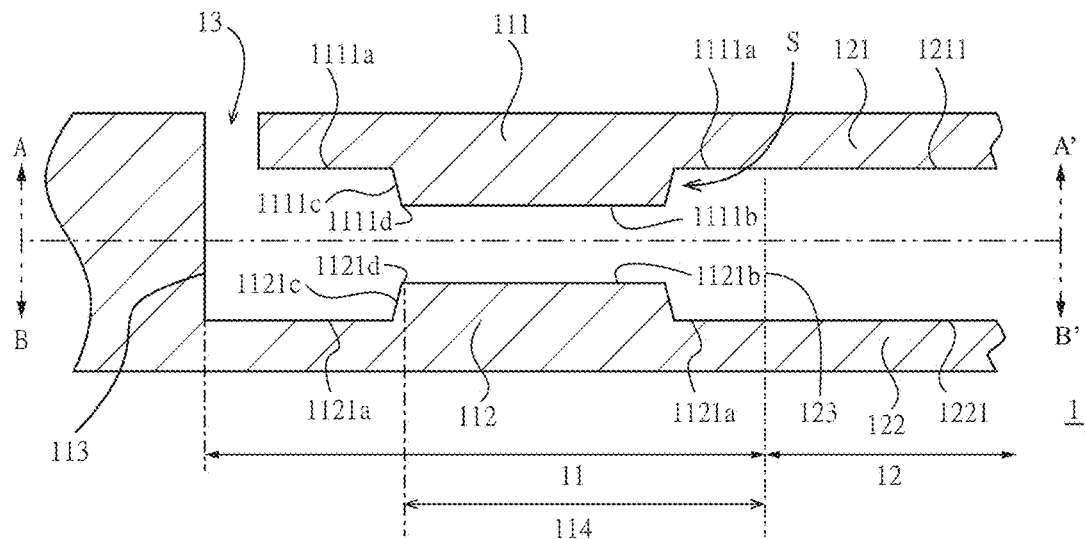
FIG. 1(a) is a vertical cross-section view of a first embodiment of a fluid inspection device in the present invention.
Figure 1B:
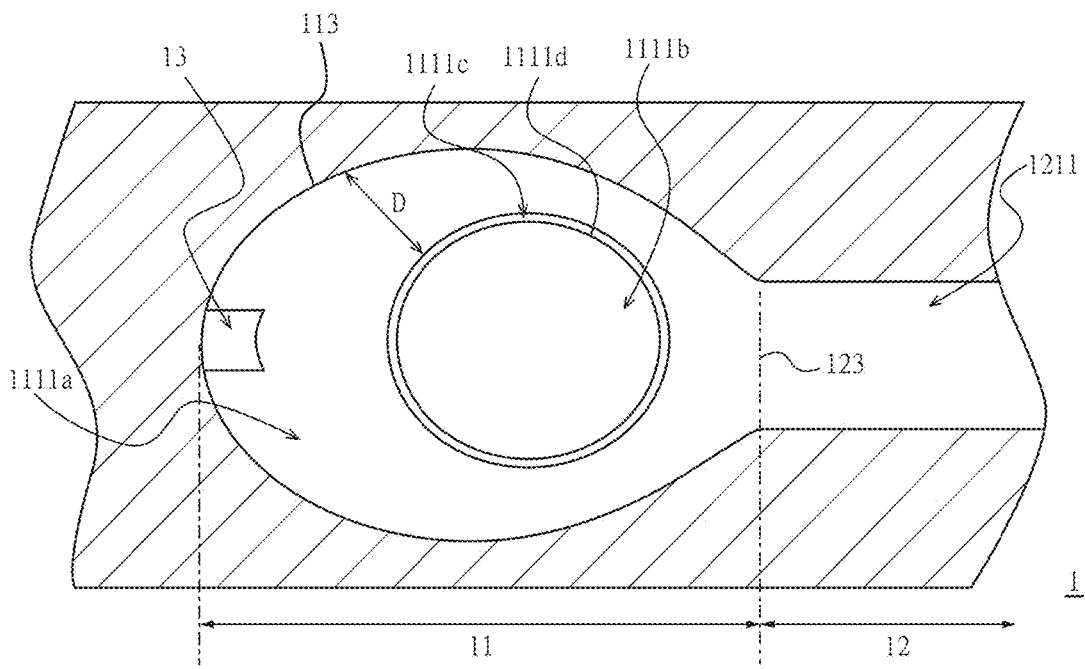
FIGS. 1(b) and 1(c) are respectively cross-section views according to cutting lines A-A' and B—B' in FIG. 1(a).
Figure 1C:
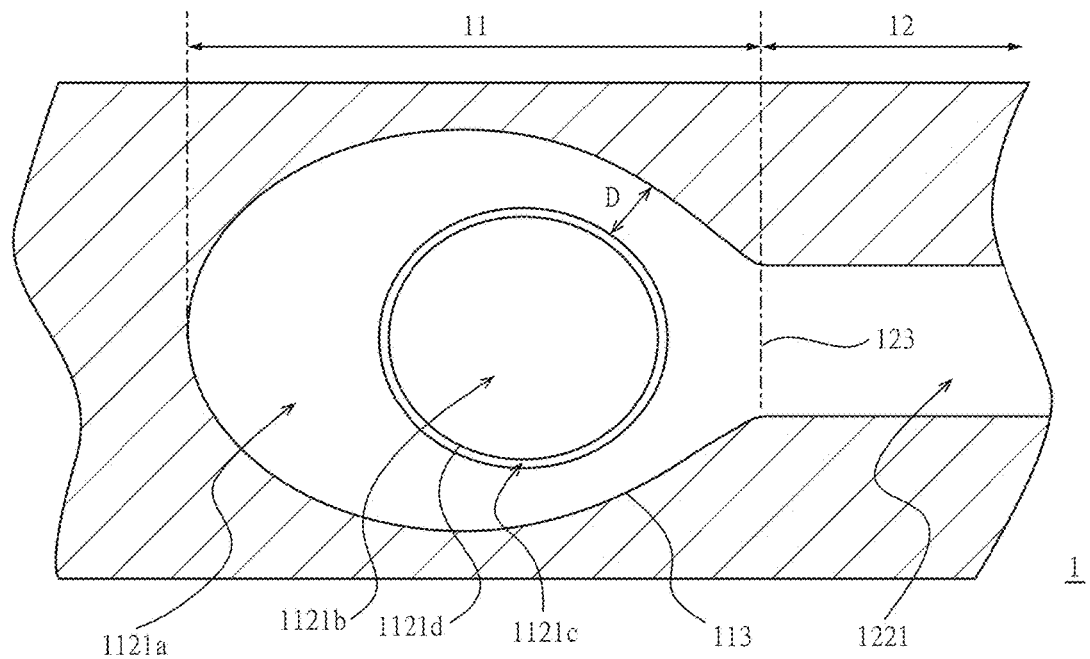

Please refer to FIGS. 1(a), 1(b) and 1(c), which are a vertical cross-section view of a first embodiment of a fluid inspection device in the present invention and cross-section views according to cutting lines A-A' and B-B' in FIG. 1(a) respectively. In the first embodiment of the present invention, the fluid inspection device 1 comprises a chamber 11, a channel 12 and a through hole 13, wherein the chamber 11 includes a top chamber portion 111, a bottom chamber portion 112 and a lateral wall 113, and the channel 12 includes a top channel portion 121, a bottom channel portion 122 and a channel end 123. The top chamber portion 111 joins the top channel portion 121, the bottom chamber portion 112 joins the bottom channel portion 122, and the chamber 11 interconnects the channel 12 through the channel end 123. The top chamber portion 111 includes a top chamber surface 1111 and the bottom chamber portion 112 includes a bottom chamber surface 1121, wherein the top chamber surface 1111 includes a top sub surface 1111a, top protruding surface 1111b and a join surface 1111c, and the bottom chamber surface 1121 includes a bottom sub surface 1121a, a bottom protruding surface 1121b and a join surface 1121c. The top channel portion 121 includes a top channel surface 1211, and the bottom channel portion 122 includes a bottom channel surface 1221. The join surface 1111c is a surface extending from the top protruding surface 1111b of the top chamber surface 1111, and the join surface 1121c is a surface extending from the bottom protruding surface 1121b of the bottom chamber surface 1121. The join surface 1111c and the join surface 1121c are the surfaces of the top chamber surface 1111 and the bottom chamber surface 1121 respectively around a fluid-filling area 114. Each of steps S is formed between the top protruding surface 1111b and the join surface 1111c and between the bottom protruding surface 1121b and the join surface 1121c respectively. The join surface 1111c can also be named as a step surface. As shown in FIGS. 1(b) and 1(c), the step surface is a surrounding surface. Moreover, the top protruding surface 1111b joins the top sub surface 1111a through the join surface 1111c and there is an edge 1111d at the junction between the top protruding surface 1111b and the join surface 1111c; and the bottom protruding surface 1121b joins the bottom sub surface 1121a through the join surface 1121c and there is an edge 1121d at the junction between the bottom protruding surface 1121b and join the surface 1121c.

Figure 2:
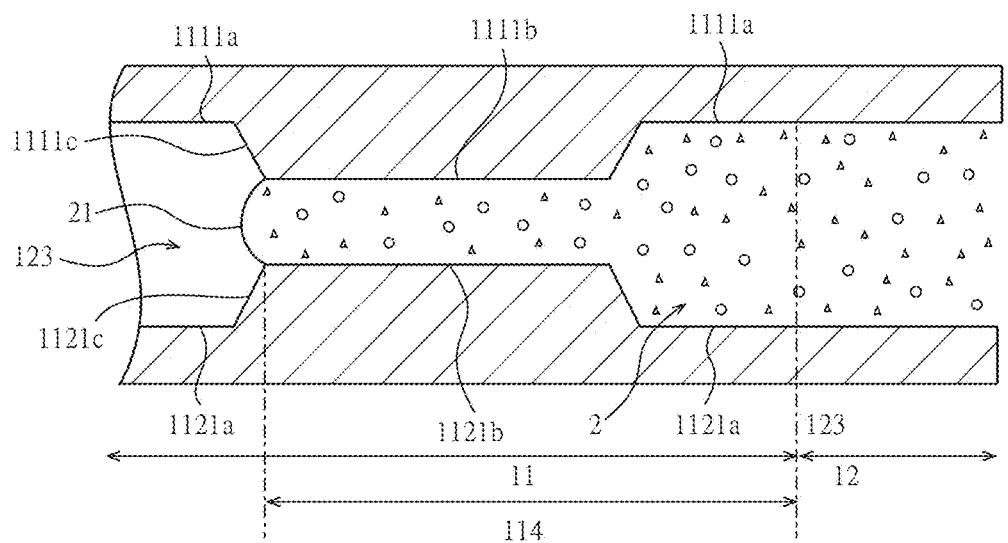
FIG. 2 is a schematic diagram of the fluid inspection device illustrating a fluid entering into a chamber from a channel.

Please refer to FIG. 2, which is a schematic diagram of the fluid inspection device 1 illustrating a fluid entering into the chamber from the channel. A tested fluid 2 (which is a liquid analyte, e.g., blood, urine, DNA, allergen or a chemical) passes from the channel 12 of the fluid inspection device 1 through the channel end 123 and enters into the chamber 11 to carry out a variety of actions, e.g. reaction or mixing. The chamber 11 may be a reaction chamber or a mixing chamber. The top chamber portion 111 and the bottom chamber portion 112 of the chamber 11 are preferably made of a material with good transparency so as to facilitate an optical inspection for the tested fluid 2.

After the tested fluid 2 from the channel 12 enters into the chamber 11, in order to prevent the air in the chamber 11 from forming bubbles and being retained in the chamber 11 to influence the course and result of the inspection resulting from that the air in the chamber 11 is exhausted slowly or cannot be exhausted out of the through hole 13, the top protruding surface 1111b and the bottom protruding surface 1121b are configured in the area within the chamber 11 where the bubbles are easy to come up to make the section of the chamber 11 smaller than that of the channel 12 so as to generate a larger capillary force to draw and expand the tested fluid 2 from the channel end 123 into the chamber 11 and then to constrain it within a desired region, which is the fluid-filling area 114. The desired region can be used as an inspection area of the tested fluid 2. Since the spacing H2 between the top protruding surface 1111b and the bottom protruding surface 1121b is smaller than the spacing H1 between the top chamber surface 1211 and the bottom channel surface 1221, the tested fluid 2 is drawn faster in this range. Furthermore, the lateral wall 113 of the chamber 11 is spaced from the fluid-filling area 114. In this embodiment, an outer periphery of the fluid-filling area 114 is substantially composed of the join surface 1111c joined to the top protruding surface 1111b and the join surface 1121c joined to the bottom protruding surface 1121b. Additionally, the outer periphery is spaced from the lateral wall 113 with a spacing D so as to make the lateral wall 113 not to generate an adhesion force toward the tested fluid 2 entering the chamber 11 as it can so as to prevent the flow of the tested fluid 2 from being influenced. Therefore, the air in the chamber 11 can be exhausted smoothly and prevent it from forming the bubbles and being retained in the chamber 11.

Moreover, because the step S structure of the top protruding surface 1111b and the bottom protruding surface 1121b can produce a constraint force to the tested fluid 2 and then the tested fluid 2 can be kept within the range between the top protruding surface 1111b and the bottom protruding surface 1121b (i.e., the fluid-filling area) as it can, as shown by a fluid surface 21 in FIG. 2, such that the required amount of the tested fluid 2 can be adjusted or diminished.

Figure 3A:
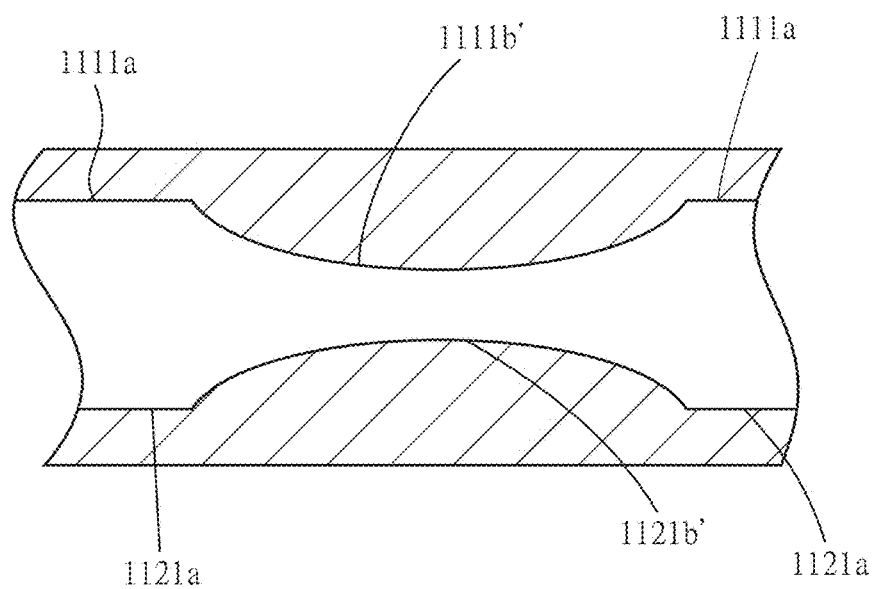
FIGS. 3(a) and 3(b) are schematic diagrams showing other embodiments based on the embodiment in FIG. 1(a).
Figure 3B:
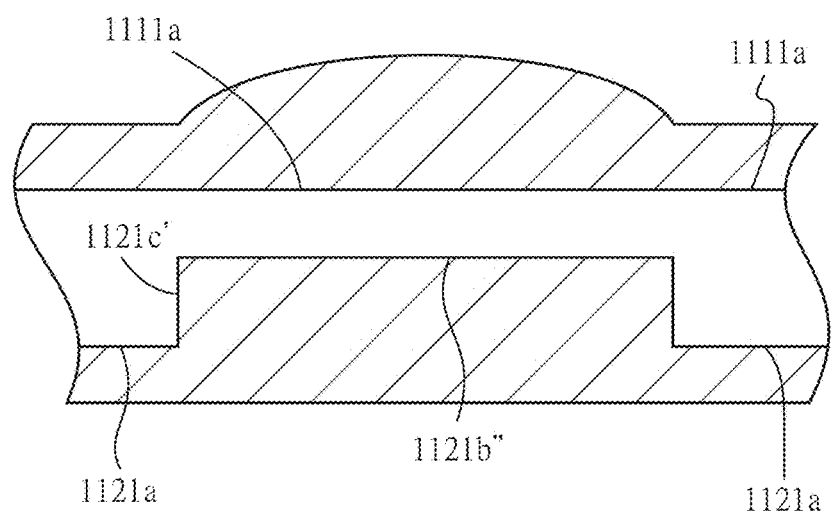

FIGS. 3(a) and 3(b) illustrate other embodiments based on the top protruding surface 1111b and the bottom protruding surface 1121b of FIG. 1(a). In FIG. 3(a), the top protruding surface 1111b' and the bottom protruding surface 1121b' are convex lenses which can provide with an additional magnification during the inspection. Alternatively, the convex structure can be configured additionally on the plane protruding surfaces such as 1111b and 1121b in FIG. 1(a). In FIG. 3(b), the chamber 11 has a plane bottom protruding surface 1121b" vertical to a join surface 1121c' and then the convex structure is formed on the outer surface of the top chamber portion 111 opposite to the bottom protruding surface 1121b". Furthermore, the join surface 1111c of the top protruding surface 1111b and the join surface 1121c of the bottom protruding surface 1121b can be formed as a one-step surface (as the above-mentioned embodiment), a multi-step surface or a curved surface. The top protruding surface 1111b and the bottom protruding surface 1121b in the embodiments of the present invention are not limited to the types shown in the figures.

Figure 4:
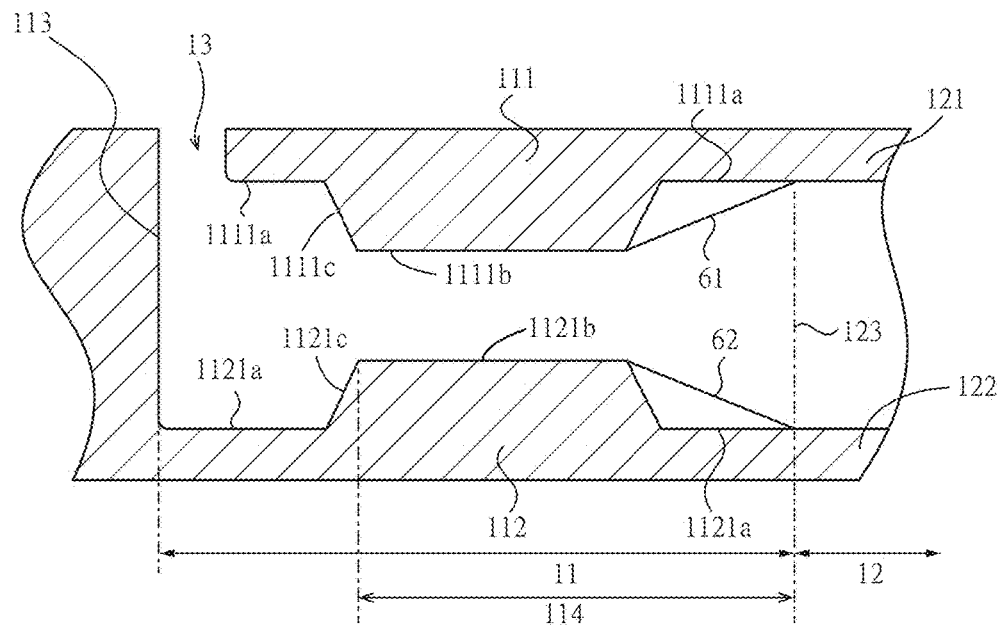
FIG. 4 is a vertical cross-section view of another embodiment with guiding surface structures based on the embodiment in FIG. 1(a).

Referring to FIG. 4, to diminish the possibility that the tested fluid 2 is drawn by the adhesion force produced by the lateral wall 113 of the chamber 11 at a very beginning and then flows along the lateral wall 113 of the chamber 11 to cause the bubbles formation, or the possibility that the tested fluid 2 flows toward a non-inspection area, the guiding surface structures 61 and 62 with descending sections can be further respectively configured between the channel end 123 and the top protruding surface 1111b in the chamber 11, and between the channel end 123 and the bottom protruding surface 1121b in the chamber 11. The guiding surface structures 61 and 62 can assist the tested fluid 2 to enter the range of the fluid-filling area 114 at the moment that the tested fluid 2 just enters into the chamber 11.

Figure 5:
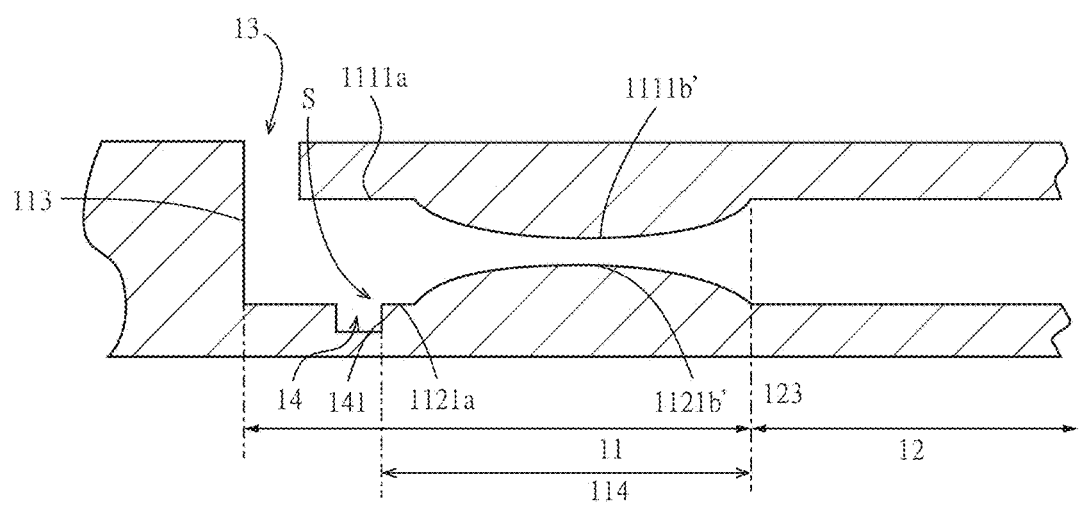
FIG. 5 is a schematic diagram showing another embodiment with a trench. This embodiment is derived from the embodiment in FIG. 1(a).

Referring to FIG. 5, when the top protruding surface 1111b' and the bottom protruding surface 1121b' are convex structures respectively (according to FIG. 3(a)), a trench 14 around the bottom protruding surface 1121b' is formed on the bottom sub surface 1121a of the bottom chamber surface 1121 near to the bottom protruding surface 1121b'. The trench 14 has a trench wall 141. The trench wall 141 and the bottom sub surface 1121a near to the bottom protruding surface 1121b' jointly form a step S to further constrain the tested fluid and then to constitute the fluid-filling area 114. The shapes of the trench 14 are not limited to this embodiment. For example, the trench 14 can be a trench with a V shape section. Moreover, the trench 14 can be configured on the top sub surface 1111a of the top chamber surface 1111 near to the top protruding surface 1111b'. The structure of the step S can also be formed on any one of or both of the top chamber surface 1111 and the bottom chamber surface 1121.

Figure 6A:
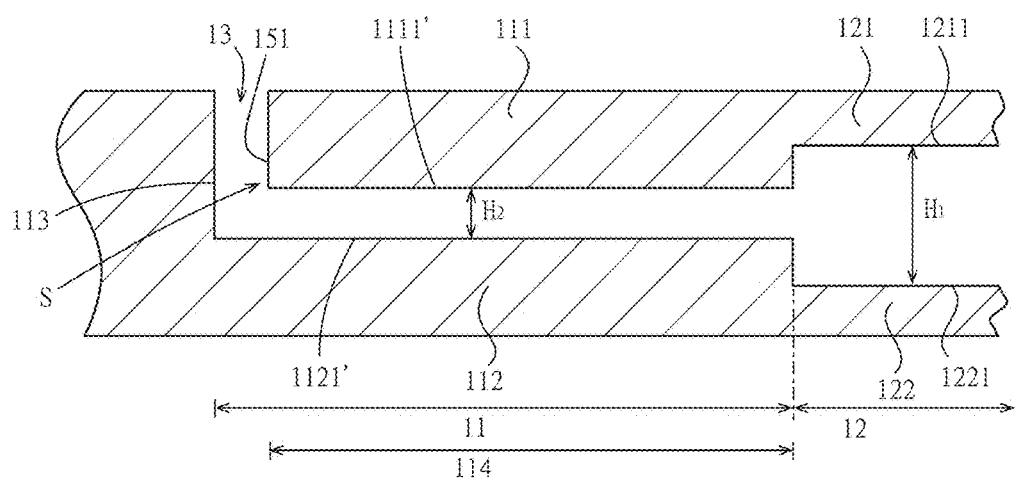
FIGS. 6(a) to 6(c) are other embodiments based on the embodiment in FIG. 1(a).
Figure 6B:
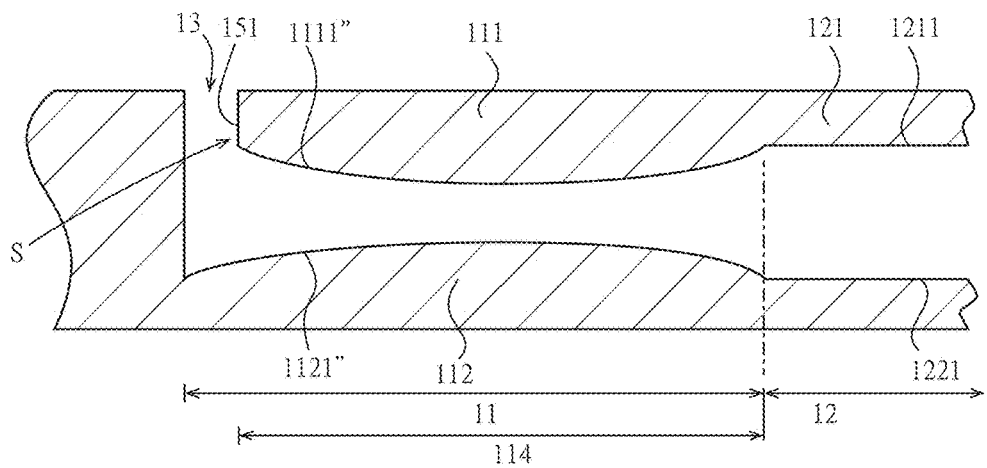
Figure 6C:
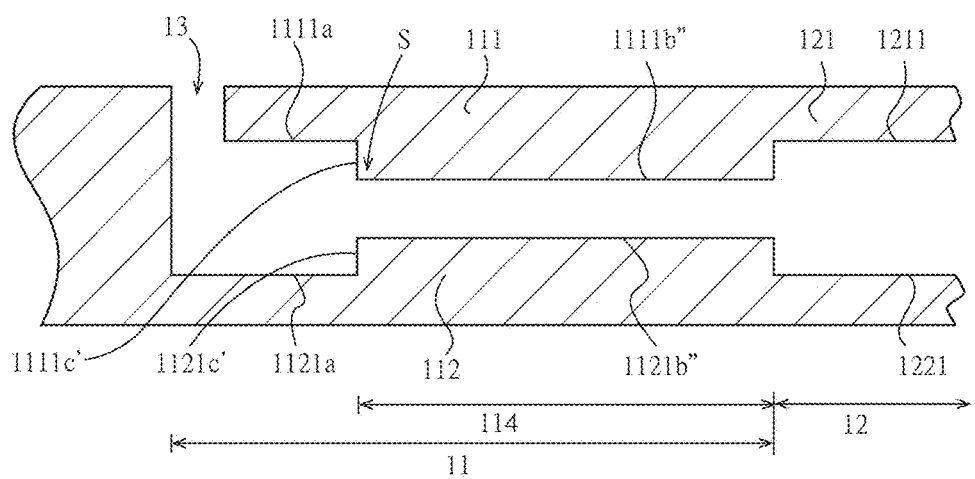

Referring to FIGS. 6(a) to 6(c), which are other embodiments of the top chamber surface 1111 and the bottom chamber surface 1121. In FIG. 6(a), the top protruding surface covers all of the top chamber surface 1111' and the bottom protruding surface covers all of the bottom chamber surface 1121'. In FIG. 6(b), the top protruding surface covers all of the top chamber surface 1111" and the bottom protruding surface covers all of the bottom chamber surface 1121". Those structures form the sections narrower than that of the channel. That is, the spacing H2 between the top chamber surface 1111' and the bottom chamber surface 1121', or between the top chamber surface 1111" and the bottom chamber surface 1121" is smaller than the spacing H1 between the top channel surface 1211 and the bottom channel surface 1221. In FIGS. 6(a) and 6(b), a step S can be formed jointly with the lateral wall 151 and one of the top chamber surfaces 1111' and 1111" to restrain the tested fluid 2 and then to form the fluid-filling area 114. In FIG. 6(c), the top protruding surface 1111b" and the bottom protruding surface 1121b" constitute a section narrower than that of channel. One step S is formed with the join surface 1111c' and the top protruding surface 1111b" jointly, and another step S is formed with the join surface 1121c' and the bottom protruding surface 1121b" jointly to restrain the tested fluid 2 and then to form the fluid-filling area 114.

In all the embodiments of the present invention abovementioned, the protruding surface can be configured only on the top chamber surface or on the bottom chamber surface, or be configured on both of the top chamber surface and the bottom chamber surface. As long as the spacing H2 between the top chamber surface and the bottom chamber surface is smaller than the spacing H1 between the top channel surface and the bottom channel surface, the structures is not limited to those shown in the figures. Additionally, the chamber disclosed in the present invention can further communicate or interconnect with other channels, chambers or components, and the structure and connection of the chamber is not limited to those shown in the figures.

Figure 7:
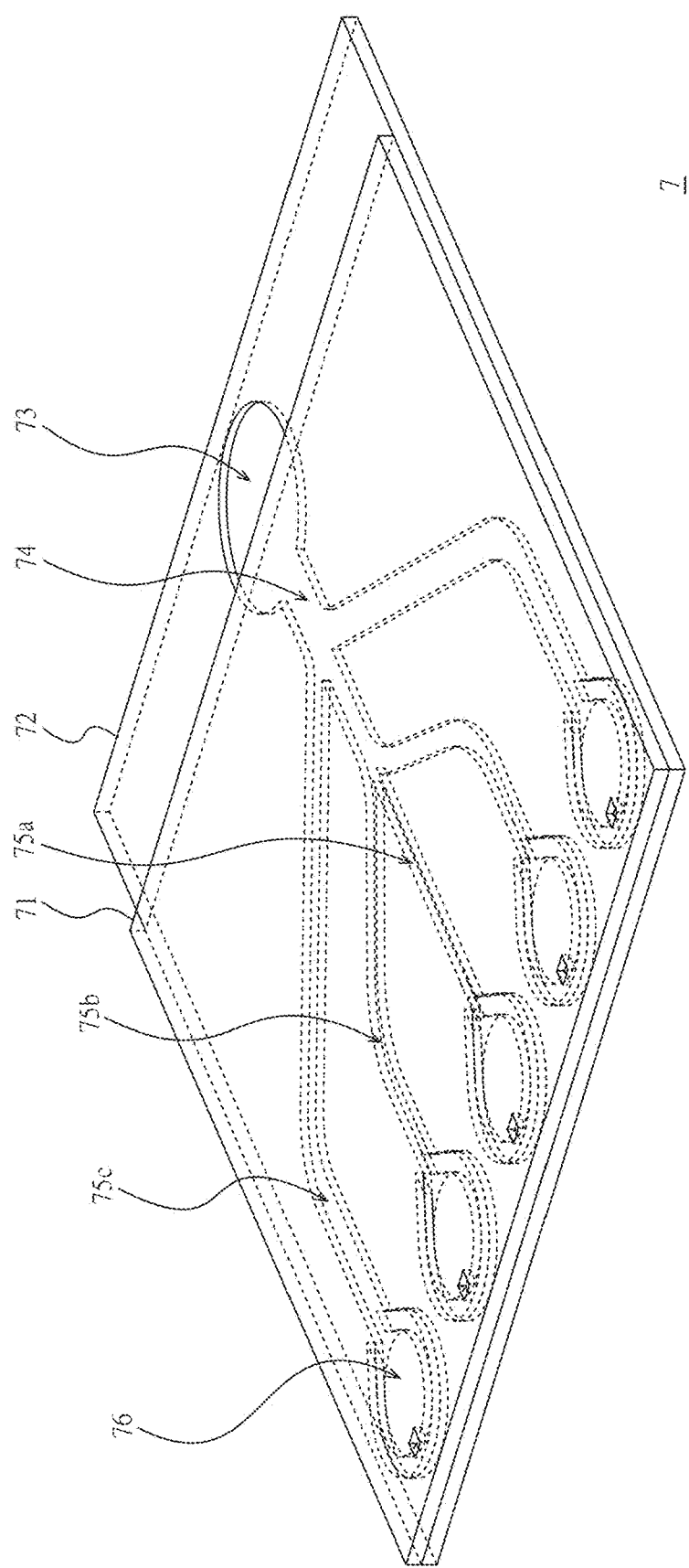
FIG. 7 is a schematic diagram showing a second embodiment of the present invention.

Please refer to FIG. 7 which is a schematic diagram showing a second embodiment according to the present invention. The second embodiment is a fluid inspection device 7 having a plurality of channels and a plurality of chambers. For example, the fluid inspection device 7 may be a test strip. The fluid inspection device 7 includes a test strip main body essentially composed of a first sheet 71 and a second sheet 72, and comprises a fluid-containing trough 73, a main channel 74, sub channels 75a, 75b and 75c and a plurality of chambers 76, wherein the fluid-containing trough 73 is connected to the main channel 74, the main channel 74 is respectively connected to the respective ends of the sub channels 75a, 75b and 75c, and the other ends (terminals) of the sub channels 75a, 75b and 75c are respectively connected to the corresponding chambers 76. The structure of the test strip is not limited to that as shown in the figure, and the test strip can be a one-piece, two-piece or multi-piece structure. In addition, the fluid inspection device according to the present invention, taking the test strip as an example, can have only one channel and only one corresponding chamber, and the structure of the fluid inspection device according to the present invention can also be applied to other inspecting devices besides the test strip.

Figure 8A:
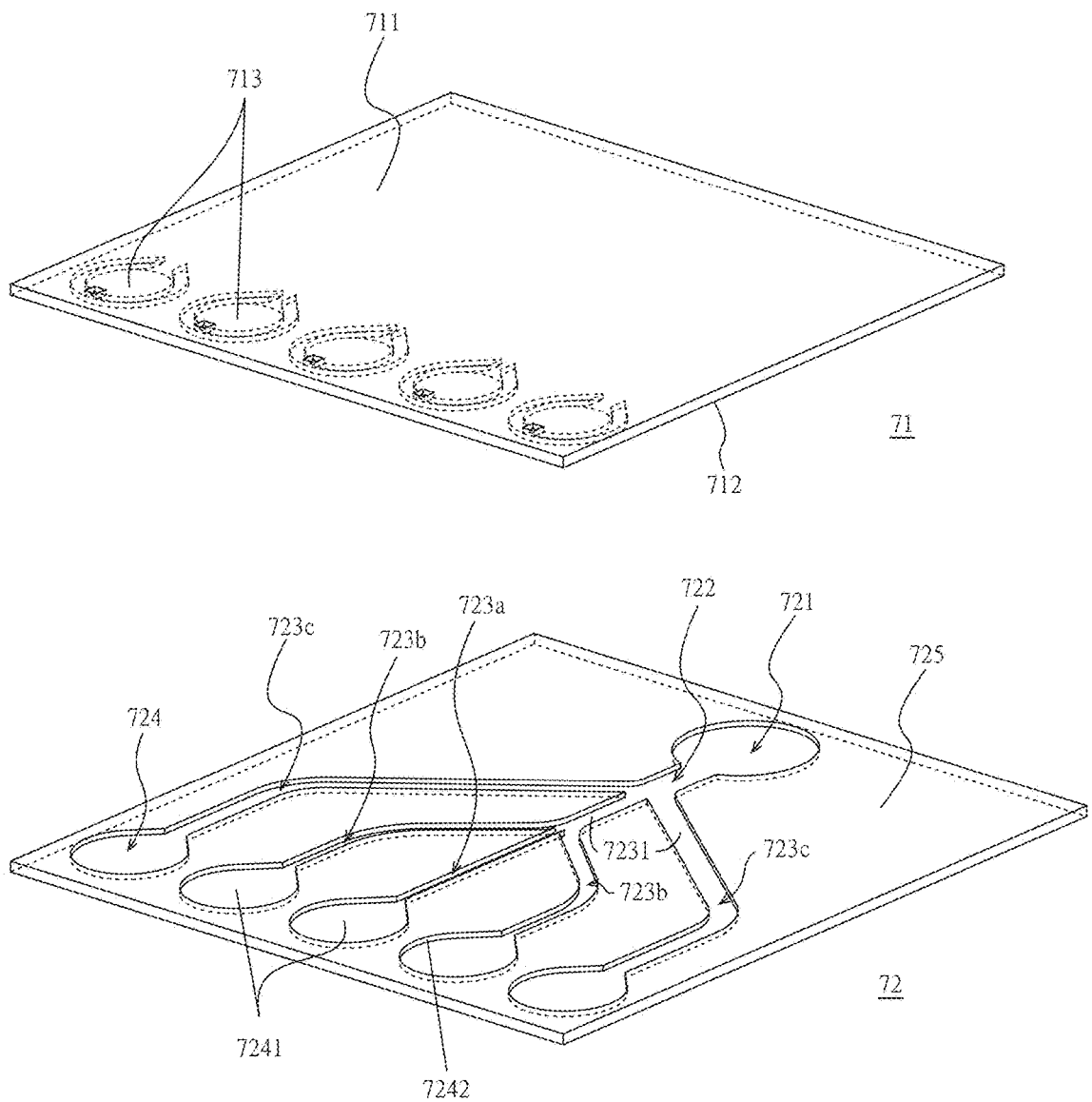
FIG. 8(a) is an exploded diagram of the embodiment in FIG. 7.
Figure 8B:
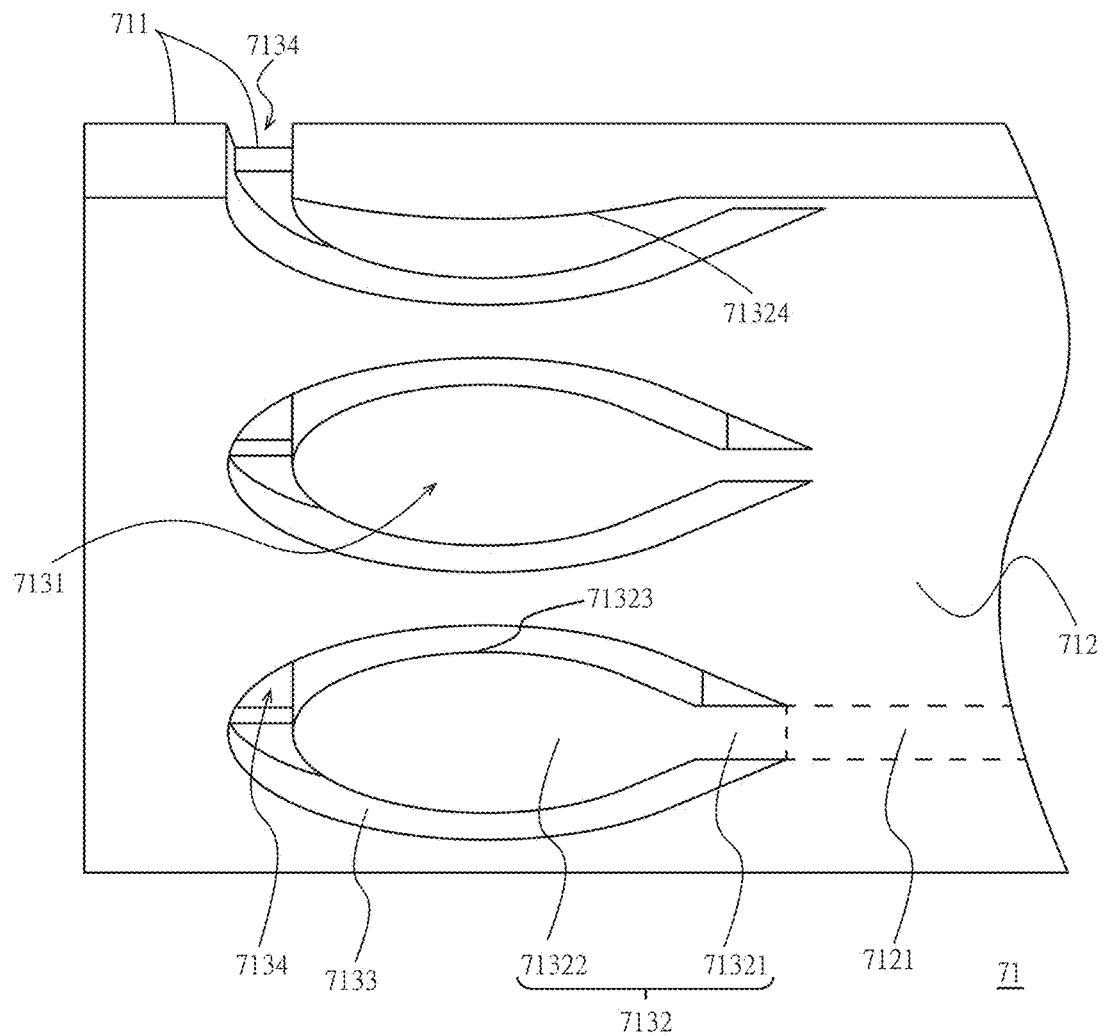
FIG. 8(b) is a perspective view of a first sheet of the second embodiment in FIG. 8(a) viewing from bottom.

Please refer to FIGS. 8(a) and 8(b) which are an exploded view of the second embodiment in FIG. 7 and a perspective view of the inner surface of the first sheet respectively. In FIG. 8(a), the first sheet 71 has a first surface 711 and a second surface 712 (in this embodiment, the first surface 711 is an outer surface of the sheet 71 and the second surface 712 is an inner surface of the first sheet 71), and includes a plurality of top chamber portions 713 configured linearly, wherein each of the top chamber portions 713 is formed by the second surface 712, and has a top chamber surface 7131, and includes a fluid-filling forming piece 7132 and a groove 7133. The fluid-filling forming piece 7132 extends from a terminal of the top sub channel portion in the first sheet 71 and has a stem portion 71321 and a circular main portion 71322. The shape of the circular main portion 71322 is not limited to a circle and can be a rhombus, an ellipse, an asymmetrical shape or other shapes. The fluid-filling forming piece 7132 is surrounded by the groove 7133 (which is designed to have a horseshoe shape in this embodiment), the groove 7133 is configured to be recessed on a rear end of the second surface 712 of the first sheet 71, and a through opening 7134 can be configured at an arbitrary position of the groove 7133 so as to communicate the chamber 76 with the outside. In the embodiment, the through opening 7134 is preferably configured at a position (as shown in FIG. 8(a)) opposite to the terminal of the sub channel on the first surface 711 of the first sheet 71. The second sheet 72 includes a bottom of the fluid-containing trough 721, a bottom main channel portion 722, bottom sub channel portions 723a, 723b and 723c and a plurality of bottom chamber portions 724, wherein these bottom portions are configured to be recessed on an upper surface 725 of the second sheet 72 to be concave chambers and channels respectively. Each of the bottom channel portions has a bottom channel surface 7231, and each of the bottom chamber portions 724 has a bottom chamber surface 7241, wherein the internal diameters (widths) of the bottom sub channel portions 723a, 723b and 723c are in an ascending order and the lengths thereof are in an ascending order as well.

As shown in FIG. 7, when the first sheet 71 and the second sheet 72 are combined together, the top chamber portions 713 and the corresponding bottom chamber portions 724 form the chambers 76 respectively. Each of the chambers 76 has a lateral wall 761 (as shown in FIG. 9(c)), which is formed together by a recessed wall 71331 of the top chamber portions 713 and a wall 7242 of the bottom chamber portion 724. There is an interval between a periphery 71323 of the fluid-filling forming piece 7132 and the lateral wall 761, and the interval is the width of the groove 7133. The interval prevents the lateral wall 761 from generating an adhesive force as it can toward the fluid flowing into the chamber 76. The bottom of the fluid-containing trough 721, the bottom main channel portion 722 and the bottom sub-channel portions 723a, 723b and 723c of the second sheet 72, and the second surface 712 (facing toward the second sheet 72) of the first sheet 71 constitute the fluid-containing trough 73, the main channel 74 and the sub channels 75a, 75b and 75c. The top channel surfaces 7121 of the top channel portions are formed by the second surface 712 of the first sheet 71. There is a first spacing H1 between a top channel surface 7121 and a bottom channel surface 7231. Because the first sheet 71 is smaller than the second sheet 72, an opening for the injection of the tested fluid is formed at a front portion 731 of the fluid-containing trough 73 by partially exposing the bottom of the fluid-containing trough 721. The rear portion 732 of the fluid-containing trough 73 is covered by the first sheet 71 to facilitate the fluid being absorbed into the main channel 74. The first sheet 71 and the second sheet 72 are preferably made from transparent materials to facilitate testing and analyzing the sample in an optical manner. The top chamber surface 7131 of the top chamber portions 713 is opposite to the bottom chamber surface 7241 of the bottom chamber portions 724. The top chamber portions 713, the bottom chamber portions 724, the structures of the bottom channel portions and the top channel portions formed on the first sheet 71 and the second sheet 72 can be exchanged. Alternatively, the structure of the fluid-filling forming piece 7132 may be formed both on the top chamber portions 713 and the bottom chamber portions 724.

Figure 9A:
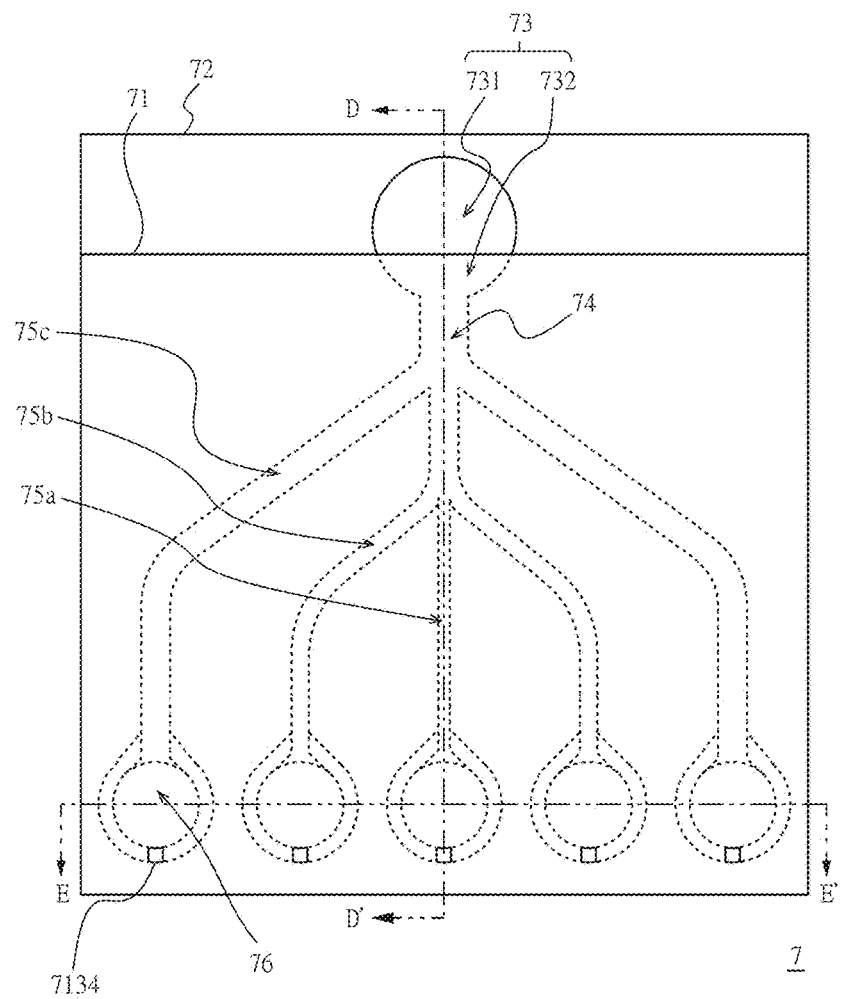
FIG. 9(a) is a top view of the embodiment in FIG. 7.
Figure 9B:
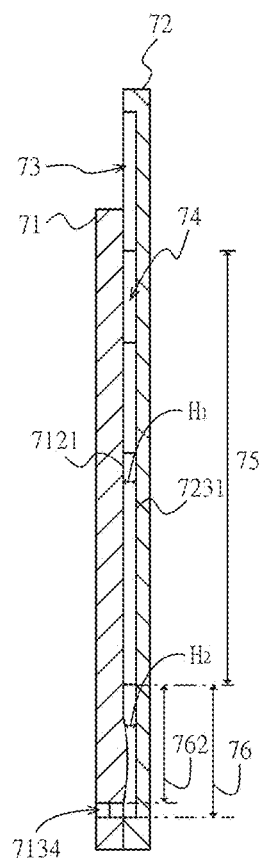
FIGS. 9(b) and 9(c) are respectively cross-section views according to the cutting lines D-D' and E-E' in FIG. 9(a).
Figure 9C:
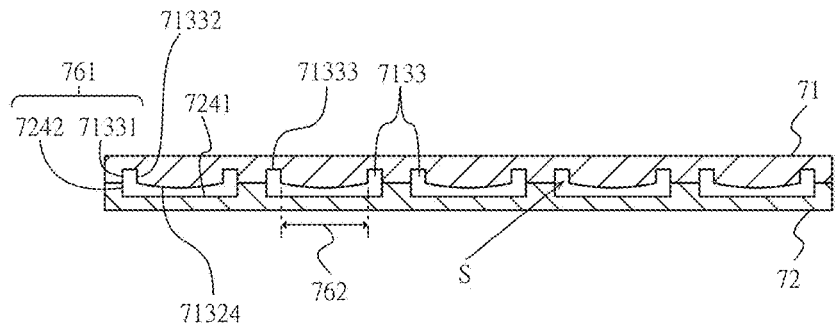

Please refer to FIGS. 9(a), 9(b) and 9(c) which are a top view of the second embodiment in FIG. 7, cross-sectional views according to cutting lines D-D' and E-E' in FIG. 9(a) respectively. The chamber 76 has a fluid-filling area 762, which is defined by the fluid-filling forming piece 7132 of the first sheet 71 and the corresponding bottom chamber portions 724 of the second sheet 72 and is surrounded by the groove 7133. In the embodiment, the inner surface of the circular main portion 71322 of the fluid-filling forming piece 7132 has a protruding paraboloid 71324 to form a portion of the top chamber surface 7131 of the fluid-filling area 762 (in this embodiment, the top chamber surface 7131 includes the inner surface of the stem portion 71321, the paraboloid 71324 and a top surface 71333 of the groove 7133). The paraboloid 71324 not only forms an optical lens to assist in optically focusing inspection, but also makes the portion of the top chamber surface 7131 of the fluid-filling area 762 and the corresponding bottom chamber surface 7241 have a second spacing H2, wherein the second spacing H2 is smaller than the first spacing H1 of each of the channels, which means that the circular main portion 71322 of the fluid-filling forming piece 7132 forms a structure with a descending section. In other embodiments, the stem portion 71321 of the fluid-filling forming piece 7132 can also form a structure with a space-descending section to facilitate generating a stronger capillary force when the fluid enters into the chamber 76 from the respective terminals of the sub channels so as to achieve a better effect. In addition, a predetermined region, where bubbles are easily generated in the chamber 76, can be chosen for this fluid inspection device to form the structure with a space-descending section, and it is not limited to the region of the whole circular main portion 71322. For example, the structure with the space-descending section can be formed at the front portion of the circular main portion 71322, and the scheme of the predetermined region may be varied based on the shape and size of the chamber 76 or the size of the internal diameter of the channel.

After the tested fluid is injected into the fluid-containing trough 73, it is drawn into the main channel 74, and then flows into the sub channels 75a, 75b and 75c, and eventually into the corresponding chambers 76 respectively. When the tested fluid flows in to the corresponding chambers 76 from the terminals of the sub channels respectively, a stronger capillary force is generated because at least a partial section (i.e., the paraboloid 71324 of the main circular portion 71322 of the fluid-filling forming piece 7132) of the fluid-filling area 762 has the space-descending section (e.g., the central portion of the paraboloid 71324 as shown in FIG. 9(b)) compared with the sections of the respective sub channels. Moreover, there is an interval between the fluid-filling area 762 and the lateral wall 761 of the chamber 76 such that the air in the chamber 76 can be exhausted smoothly out of the chamber 76 via a through opening 7134 and will not be trapped in the chamber 76 to form bubbles to obstruct the inspection. Therefore, the conventional problem that the bubbles comes up easily in the center of the chamber and is hard to be exhausted can be solved. In addition, a step S is formed at the join of the groove wall 71332 of the first sheet 71 and the top chamber surface 7131 of the fluid-filling area 762 formed with the fluid-filling forming piece 7132. Owing to the step S, the tested fluid merely enters the fluid-filling area 762 of the chamber 76, and substantially stops in the fluid-filling area 762 or at most slightly oozes at the groove 7133, but does not flow into the groove 7133. Accordingly, such a design has an advantage of reducing the required amount of the tested fluid. The step S may be configured at any one or both of the bottom chamber surface 7241 of the bottom chamber portions 724 and the top chamber surface 7131 of the top chamber portions 713.

Figure 9D:
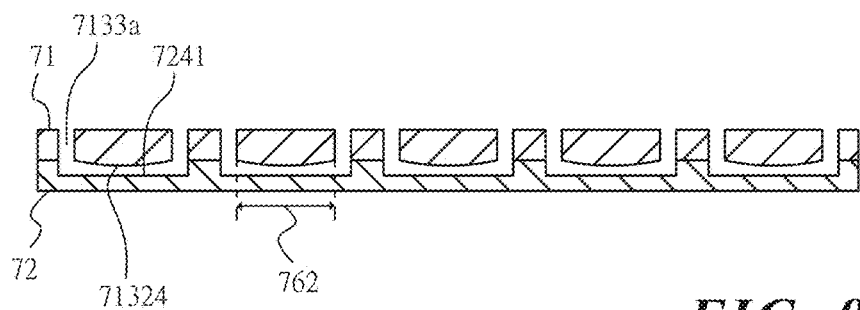
FIG. 9(d) is a cross-section view of another embodiment according to cutting line E-E' in FIG. 9(a).

Please refer to FIG. 9(d), which is a cross-section view of another embodiment according to a cutting line E-E' in FIG. 9(a). The top groove surface 71333 of the groove 7133 of the first sheet 71 is hollowed to form a through groove 7133a so as to eject the air in the chamber 76, and the other structures are the same as those in FIG. 9(c). No matter the form of the through opening in this fluid inspection device is the through opening 7134 or the through groove 7133a, there can be only one through opening configured at the test strip and communicating with the plurality of chambers. In other words, it is not limited to that each of the chambers has its corresponding through opening as shown in the figures.

Figure 9E:
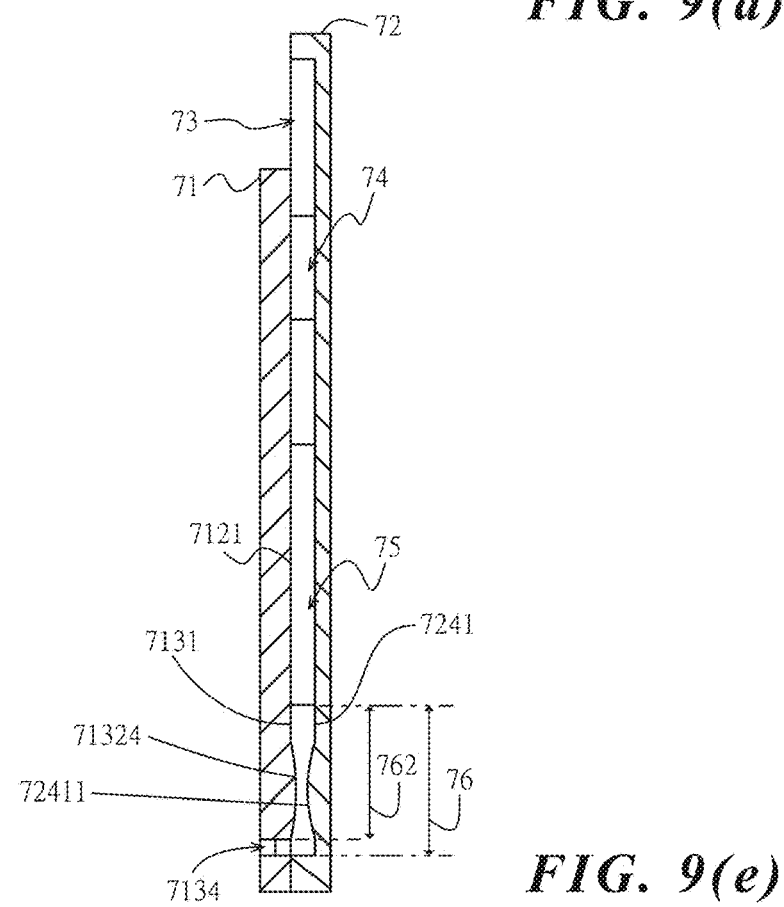
FIGS. 9(e) and 9(f) are cross-section views of a further embodiment according to cutting lines D-D' and E-E' in FIG. 9(a) respectively.
Figure 9F:
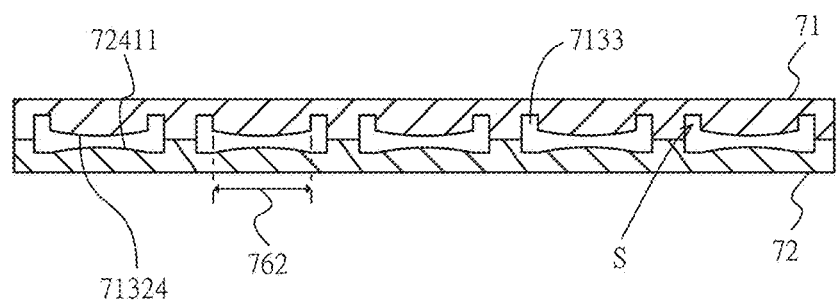

Please refer to FIGS. 9(e) and 9(f), which are cross-section views of another embodiment according to cutting lines D-D' and E-E' in FIG. 9(a) respectively. The paraboloid 72411 is configured on the bottom chamber surface 7241, and corresponding to the paraboloid 71324 on the circular main portion 71322 of the fluid-filling forming piece 7132. The other structures are the same as those in FIGS. 9(*b*) and 9(*c*).

Figure 10A:
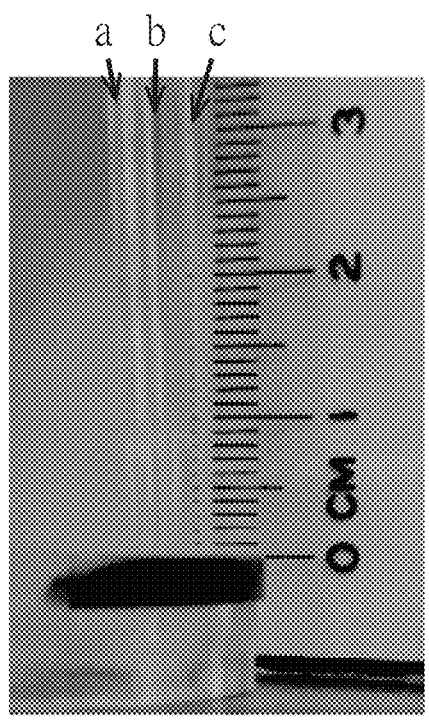
FIG. 10(a) is a video record taken at the beginning of an experiment.
Figure 10B:
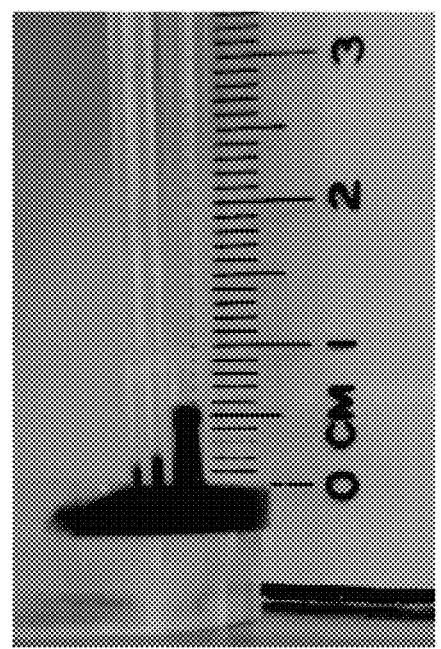
FIGS. 10(b) and 10(c) are the video records taken at 0.2 and 5.2 seconds after beginning of the experiment respectively.
Figure 10C:
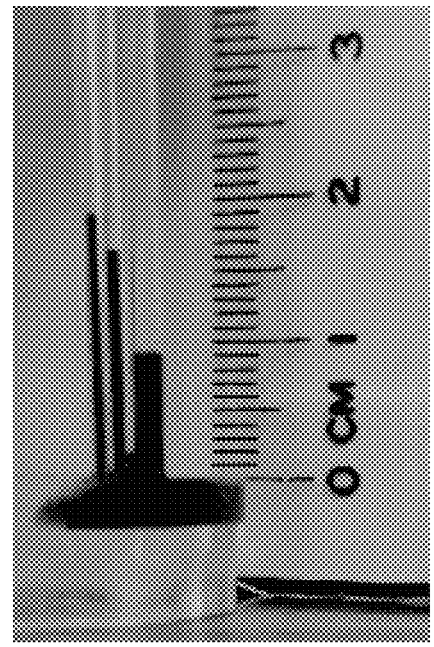

An experiment is conducted with three vertically configured capillary tubes a, b and c. The internal diameters of the capillary tubes a, b and c are in a descending order, and the ratio of the internal diameters of the capillary tubes a, b and c is 1.00:0.57:0.39. After the bottoms of the capillary tubes a, b and c are aligned and then they simultaneously contact the surface of a blood. The states of rising of the liquid columns are recorded. Please refer to FIGS. 10(*a*) to 10(*c*), which are the pictures showing the video record after 0, 0.2 and 5.2 seconds from the start of recording respectively. The larger the internal diameter of the capillary tube, the smaller a resistance force, so that the flow rate of the blood is higher. The smaller the internal diameter of the capillary tube, the greater the resistance force, so that the flow rate of the blood is lower. Accordingly, after the respective capillary tubes contact the blood for 0.2 second, the height ratio of the surfaces of the blood in the capillary tubes a, b and c is 1.00:1.76:2.06 as shown in FIG. 10(*b*). When the respective capillary tubes contact the blood for 5.2 seconds, the liquid columns in the respective capillary tubes almost do not rise as shown in FIG. 10(*c*). At this time, due to the greater capillary force, the surface of the blood in the capillary tube with the smaller internal diameter will be dragged higher. According to the result of the experiment, the multi-channels of the fluid inspection device 7 can be designed on demand, wherein the channels 74, 75*a*, 75*b* and 75*c* are radially configured, the path of the middle channel 75*a* is shorter, and the diameter of the channel 75*a* is designed to be thinner; the paths of the channels 75*b* and 75*c* on both sides are even longer when the channel 75*b* and the channel 75*c* are located outward, and the diameters of the channels 75*b* and 75*c* are designed to be thicker, so as to make the flow rate higher, so that the fluid in the all channels of the fluid inspection device 7 can enter into the corresponding chambers 76 substantially at the same time so as to facilitate processing the inspection. The configuration of the multi-channels and the multi-chambers of the fluid inspection device of the present invention is not limited to the configuration as shown in the embodiments, and it can be designed on demand.

The invention need not be limited to the disclosed embodiments and the wording/terms, and it is intended to cover various modifications and similar arrangements included within the spirit of the present invention and the scope of the appended claims.

What is claimed is:

1. A fluid inspection device, comprising:
   at least one channel including a top channel surface and a bottom channel surface, wherein a first spacing is formed therebetween;
   at least one chamber communicating with the at least one channel from which a fluid flows into the at least one chamber and including a top chamber surface, a bottom chamber surface and a fluid-filling area, the fluid-filling area is a portion of the at least one chamber filling with the fluid communicating with the at least one channel, wherein a second spacing is formed between the top chamber surface of at least a portion of the fluid-filling area and the bottom chamber surface corresponding to the at least a portion of the fluid-filling area; and
   a through opening communicating with the at least one chamber and an outside of the fluid inspection device, the second spacing of the at least one chamber is smaller than the first spacing of the at least one channel,
   wherein the top chamber surface comprises a top sub surface, a top protruding surface and a first join surface connecting the top sub surface and the top protruding surface, and a first step is formed between the top protruding surface and the first join surface,
   the bottom chamber surface comprises a bottom sub surface, a bottom protruding surface and a second joint surface connecting the bottom sub surface and the bottom protruding surface, and a second step is formed between the bottom protruding surface and the second join surface.

2. The fluid inspection device as claimed in claim 1, wherein a surface is formed at least one of the top chamber surface and the bottom chamber surface around the fluid-filling area to form a step between the surface and at least one of the top chamber surface and the bottom chamber surface of the at least a portion of the fluid-filling area.

3. The fluid inspection device as claimed in claim 2, wherein the at least one chamber further includes a lateral wall connected to at least one of the top chamber surface and the bottom chamber surface, and a spacing is formed between the lateral wall and a periphery of the fluid-filling area.

4. The fluid inspection device as claimed in claim 2, wherein at least one of the top chamber surface and the bottom chamber surface of the at least a portion of the fluid-filling area has a paraboloid.

5. A fluid inspection device, comprising:
   a test strip, including:
   a plurality of channels, each of which includes a top channel surface and a bottom channel surface, wherein a first spacing is formed therebetween;
   a plurality of chambers respectively communicating with the plurality of channels from which a fluid flows into the plurality of chambers, wherein each of the plurality of chambers includes a top chamber surface, a bottom chamber surface and a fluid-filling area, the fluid-filling area is a portion of the at least one chamber filling with the fluid communicating with the at least one channel and a second spacing is formed between the top chamber surface of at least a portion of the fluid-filling area and the bottom chamber surface corresponding to the at least a portion of the fluid-filling area; and
   at least one through opening communicating with the plurality of chambers and an outside of the fluid inspection device,
   the second spacing of the at least one chamber is smaller than the first spacing of the at least one channel,
   wherein the top chamber surface comprises a top sub surface, a top protruding surface and a first join surface connecting the top sub surface and the top protruding surface, and a first step is formed between the top protruding surface and the first join surface,
   the bottom chamber surface comprises a bottom sub surface, a bottom protruding surface and a second joint surface connecting the bottom sub surface and the bottom protruding surface, and a second step is formed between the bottom protruding surface and the second join surface.

6. The fluid inspection device as claimed in claim 5, wherein a surface is formed at least one of the top chamber surface and the bottom chamber surface around the fluid-filling area to form a step between the surface and the at least one of the top chamber surface and the bottom chamber surface of the at least a portion of the fluid-filling area.

7. The fluid inspection device as claimed in claim 6, wherein each of the plurality of chambers further includes a lateral wall connected to at least one of the top chamber surface and the bottom chamber surface, and a spacing is formed between the lateral wall and a periphery of the fluid-filling area.

8. The fluid inspection device as claimed in claim 7, wherein at least one of the top chamber surface and the corresponding bottom chamber surface of the at least a portion of the fluid-filling area in each of the plurality of chambers has a paraboloid.

9. The fluid inspection device as claimed in claim 7, wherein the test strip includes a first sheet and a second sheet, the first sheet and the second sheet are configured opposite to each other, the plurality of channels and the plurality of chambers are configured between the first sheet and the second sheet, and the at least one through opening includes a plurality of through openings configured to communicate with the plurality of corresponding chambers respectively, wherein:

the first sheet includes a plurality of top chamber portions and a plurality of top channel portions, the plurality of top chamber portions are connected to the plurality of corresponding top channel portions respectively, each of the plurality of top chamber portions has the top chamber surface and includes a first fluid-filling forming piece and a first groove, and the first fluid-filling forming piece is formed by extending from an end of the top channel portion in the first sheet and is surrounded by the first groove; and the second sheet includes a plurality of bottom chamber portions and a plurality of bottom channel portions, the plurality of bottom chamber portions are connected to the plurality of corresponding bottom channel portions respectively, and each of the plurality of bottom chamber portions has the bottom chamber surface, wherein each of the plurality of top chamber portions and each of the plurality of corresponding bottom chamber portions form each of the plurality of chambers, each of the plurality of top channel portions and each of the plurality of corresponding bottom channel portions form each of the plurality of channels, and the first fluid-filling forming piece and the corresponding bottom chamber surface form the fluid-filling area.

10. The fluid inspection device as claimed in claim 9, wherein the first groove is configured to be recessed on an inner surface of the first sheet and forms the interval between the lateral wall and the periphery of the fluid-filling area, and the step is formed between a wall of the first groove and the top chamber surface of the fluid-filling area.

11. The fluid inspection device as claimed in claim 10, wherein the first fluid-filling forming piece includes a stem portion and a main portion, the stem portion is connected to the end of the top channel portion, and a paraboloid is formed on an inner side of the main portion.

12. The fluid inspection device as claimed in claim 9, wherein the through opening is configured on the first groove, or the first groove is a through groove.

13. The fluid inspection device as claimed in claim 9, wherein the plurality of bottom chamber portions and the plurality of bottom channel portions respectively include a plurality of concave chambers and a plurality of concave channels recessed on the upper surface of the second sheet.

14. The fluid inspection device as claimed in claim 9, wherein each of the plurality of bottom chamber portions includes a second fluid-filling forming piece corresponding to the first fluid-filling forming piece and a second groove corresponding to the first groove, and the fluid-filling area is formed by the first fluid-filling forming piece and the second fluid-filling forming piece.

15. The fluid inspection device as claimed claim 5, wherein the test strip further includes a fluid-containing trough configured at one end of the test strip to fill the fluid and communicate with the plurality of channels, wherein a shorter one of the plurality of channels has a smaller width and a longer one of the plurality of channels has a larger width so that the fluid filled in the fluid-containing trough enters in the plurality of chambers at the same time via the plurality of channels respectively.

16. The fluid inspection device as claimed in claim 15, wherein the plurality of channels are radially configured, and the plurality of chambers are linearly configured at the other end of the test strip.

17. The fluid inspection device as claimed in claim 15, wherein the test strip includes a first sheet and a second sheet, the first sheet and the second sheet are configured opposite to each other, the plurality of channels and the plurality of chambers are configured between the first sheet and the second sheet, the fluid-containing trough is configured to be recessed on an upper surface of the second sheet and has a front portion and a rear portion, the front portion is an opening for the fluid to be filled in, and the rear portion is covered by the first sheet so that the fluid is absorbed into the plurality of channels.

* * * * *